US010664671B2

(12) United States Patent
Jaiswal et al.

(10) Patent No.: US 10,664,671 B2
(45) Date of Patent: May 26, 2020

(54) METHOD AND SYSTEM FOR ACTIVITY RECOGNITION AND BEHAVIOUR ANALYSIS

(71) Applicant: Tata Consultancy Services Limited, Mumbai (IN)

(72) Inventors: Dibyanshu Jaiswal, Kolkata (IN); Andrew Gigie, Kolkata (IN); Avik Ghose, Kolkata (IN); Tapas Chakravarty, Kolkata (IN); Archan Misra, Singapore (SG)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 16/434,597

(22) Filed: Jun. 7, 2019

(65) Prior Publication Data
US 2019/0377916 A1 Dec. 12, 2019

(30) Foreign Application Priority Data
Jun. 8, 2018 (IN) .............................. 201821021608

(51) Int. Cl.
*A01K 11/00* (2006.01)
*H04W 4/029* (2018.01)
(Continued)

(52) U.S. Cl.
CPC ........ *G06K 7/10366* (2013.01); *A61B 5/1113* (2013.01); *A61B 5/1114* (2013.01);
(Continued)

(58) Field of Classification Search
CPC ..... A61B 5/002; A61B 5/1113; A61B 5/1118; A61B 5/1123; A61B 5/6802;
(Continued)

(56) References Cited

U.S. PATENT DOCUMENTS 10,007,406 B1* 6/2018 Libin .................... G06F 3/0484
2014/0253504 A1* 9/2014 Noshadi ............ H04M 1/72527
345/174
(Continued)

*Primary Examiner* — Dionne Pendleton
(74) *Attorney, Agent, or Firm* — Finnegan, Henderson, Farabow, Garrett & Dunner LLP

(57) ABSTRACT

Energy remains a critical challenge for continuous sensing: with low-capacity batteries, wearable devices require frequent charging. In contrast, installing sensors in everyday 'smart objects', such as kitchen cabinets, household appliances and office equipment, supports ADL detection via indirect observations on human interaction with such objects, but cannot provide individual-specific insights in multi-tenanted environments. The embodiments herein provide a method and system for energy efficient activity recognition and behavior analysis. Architecture disclosed utilizes a hybrid mode of inexpensive, battery-free sensing of physical activities performed by a subject been monitored during his Activities for Daily Living (ADLs). The sensing combines object interaction sensing with person-specific wearable sensing to recognize individual activities in smart spaces. The method and system disclosed quantifies a probabilistic approach that uses longitudinal observations of user-item interactions, over each individual episode, to compute the anomalous behavior of the subject.

12 Claims, 8 Drawing Sheets

(51) Int. Cl.
  *G06K 7/10* (2006.01)
  *G06K 9/00* (2006.01)
  *G06F 3/01* (2006.01)
  *A61B 5/00* (2006.01)
  *A61B 5/11* (2006.01)
  *G08B 21/04* (2006.01)

(52) U.S. Cl.
  CPC ............ *A61B 5/1115* (2013.01); *A61B 5/1123* (2013.01); *A61B 5/6802* (2013.01); *G06F 3/017* (2013.01); *G06K 7/10207* (2013.01); *G06K 9/00335* (2013.01); *G08B 21/0446* (2013.01); *G08B 21/0461* (2013.01)

(58) Field of Classification Search
  CPC ... A61B 5/6889; A61B 5/6891; A61B 5/7264; A61B 5/1114; A61B 5/1115; G06F 3/011; G06F 3/017; G06K 19/0716; G06K 19/0723; G06K 7/10207; G06K 7/10366; G06K 9/00335; G06K 9/00348; G06K 9/00342; G08B 21/0423; G08B 21/0469; G08B 21/0446; G08B 21/0461; H04B 5/0062; H04W 4/029; H04W 4/80
  See application file for complete search history.

(56) References Cited

U.S. PATENT DOCUMENTS

| | | | |
|---|---|---|---|
| 2015/0355311 A1* | 12/2015 | O'Hagan | G01S 5/021 340/539.13 |
| 2016/0231109 A1* | 8/2016 | Chang | G01P 13/00 |
| 2016/0354014 A1 | 12/2016 | Lobner et al. | |
| 2017/0025152 A1* | 1/2017 | Jaime | G11B 27/11 |
| 2019/0387711 A1* | 12/2019 | Flennert | A01K 29/005 |

* cited by examiner

METHOD AND SYSTEM FOR ACTIVITY RECOGNITION AND BEHAVIOUR ANALYSIS

CROSS-REFERENCE TO RELATED APPLICATIONS AND PRIORITY

The present application claims priority from Indian provisional patent application no. 201821021608, filed on Jun. 8, 2018. The entire contents of the aforementioned application are incorporated herein by reference.

TECHNICAL FIELD

The disclosure herein generally relates to activity monitoring, and, more particularly, method and system for energy efficient activity recognition and behavior analysis.

BACKGROUND

Recognition of activities, typically the activities of daily living (ADLs) in smart home or office environments tend to utilize two distinct paradigms. The wearable sensing approach typically utilizes sensors embedded in wearable computing devices, such as smart watches and smart glasses, to capture fine-grained, individual specific locomotion and gestural activities. However, energy remains a critical challenge for continuous sensing: with low-capacity batteries, wearable devices requiring frequent charging. In contrast, installing sensors in everyday 'smart objects', such as kitchen cabinets, household appliances and office equipment, supports ADL detection via indirect observations on human interaction with such objects, but cannot provide individual-specific insights in multi-tenanted environments.

SUMMARY

Embodiments of the present disclosure present technological improvements as solutions to one or more of the above-mentioned technical problems recognized by the inventors in conventional systems. For example, in one embodiment, a method for activity recognition and behavior analysis is provided. The method includes seamlessly sensing using a Radio Frequency Identification (RFID) reader operating in a low power mode, sensor data received from at least one battery less primary sensor associated with at least one primary object, wherein usage of the at least one primary object is mandatory to initiate a primary activity associated with an ADL among a plurality of Activities of Daily Living (ADLs). The method further includes detecting mobility of a subject to initiate the primary activity based on variation in the sensor data received from the at least one battery less primary sensor associated with the at least one primary object, wherein the variation in the sensor data indicates proximity of the subject with the at least one primary object. Further, the method includes triggering the RFID reader to switch from the low power mode to a high power mode on detection of mobility of the subject for the primary activity, wherein the RFID reader in the high power mode receives RF data from: at least one battery less wearable tag worn by the subject, wherein the at least one battery less wearable tag comprises RF powered passive accelerometer; and a plurality of passive RFID tags tagged to a plurality of secondary objects placed in proximity to the at least one primary object, wherein one or more secondary objects from a plurality of secondary objects, required to be used by the subject while performing one or more secondary activities associated with each ADL among the plurality of ADLs to perform each ADL without presence of anomaly, are predefined. Furthermore, the method includes analyzing the RF data received from the at least one battery less wearable tag over a plurality of window intervals to tag the primary activity of the subject, for each window interval, to an ADL among the plurality of ADLs. Thereafter, the method includes analyzing the RF data received from the plurality of passive RFID tags of interest over each of the window interval to detect the one or more secondary activities performed by the subject using the one or more secondary objects and interaction of the subject with the one or more secondary objects corresponding to the tagged primary activity. Furthermore, the method includes and determining presence of anomaly in each window interval if the tagged primary activity of each window interval and the interaction of the subject with the one or more secondary objects in the detected one or more secondary activities for each window interval maps to a predefined primary object and secondary object usage criteria, wherein the predefined criteria is set for confirming expected execution of the ADL among the plurality of ADLs.

In another aspect, a system for activity recognition and behavior analysis is provided. The system comprises a memory storing instructions; one or more Input/Ouput (I/O) interfaces; and one or more hardware processors coupled to the memory via the one or more I/O interfaces, wherein the one or more hardware processors are configured by the instructions to: seamlessly sense using a RFID reader operating in a low power mode, sensor data received from at least one battery less primary sensor associated with at least one primary object, wherein usage of the at least one primary object is mandatory to initiate a primary activity associated with an ADL among a plurality of Activities of Daily Living (ADLs). The one or more hardware processors are further configured to detecting mobility of a subject to initiate the primary activity based on variation in the sensor data received from the at least one battery less primary sensor associated with the at least one primary object, wherein the variation in the sensor data indicates proximity of the subject with the at least one primary object. The one or more hardware processors are further configured to trigger the RFID reader to switch from the low power mode to a high power mode on detection of mobility of the subject for the primary activity, wherein the RFID reader in the high power mode receives RF data from: at least one battery less wearable tag worn by the subject, wherein the at least one battery less wearable tag comprises RF powered passive accelerometer; and a plurality of passive RFID tags tagged to a plurality of secondary objects placed in proximity to the at least one primary object, wherein one or more secondary objects from a plurality of secondary objects, required to be used by the subject while performing one or more secondary activities associated with each ADL among the plurality of ADLs to perform each ADL without presence of anomaly, are predefined. Furthermore, the one or more hardware processors are further configured to analyze the RF data received from the at least one battery less wearable tag over a plurality of window intervals to tag the primary activity of the subject, for each window interval, to an ADL among the plurality of ADLs. The one or more hardware processors are further configured to analyze the RF data received from the plurality of passive RFID tags of interest over each window interval to detect the one or more secondary activities performed by the subject using the one or more secondary objects and interaction of the subject with the one or more secondary objects corresponding to the tagged primary activity. Furthermore, one or more hardware processors are configured to determine presence of anomaly in each of the window interval if the tagged primary activity of each window interval and the interaction of the subject with the one or more secondary objects in the detected one or more secondary activities for each window interval maps to a predefined primary object and secondary object usage criteria, wherein the predefined criteria is set for confirming expected execution of the ADL among the plurality of ADLs.

In yet another aspect, there are provided one or more non-transitory machine readable information storage mediums comprising one or more instructions, which when executed by one or more hardware processors causes a method for activity recognition and behavior analysis is provided. The method includes seamlessly sensing using a RFID reader operating in a low power mode, sensor data received from at least one battery less primary sensor associated with at least one primary object, wherein usage of the at least one primary object is mandatory to initiate a primary activity associated with an ADL among a plurality of Activities of Daily Living (ADLs). The method further includes detecting mobility of a subject to initiate the primary activity based on variation in the sensor data received from the at least one battery less primary sensor associated with the at least one primary object, wherein the variation in the sensor data indicates proximity of the subject with the at least one primary object. Further, the method includes triggering the RFID reader to switch from the low power mode to a high power mode on detection of mobility of the subject for the primary activity, wherein the RFID reader in the high power mode receives RF data from: at least one battery less wearable tag worn by the subject, wherein the at least one battery less wearable tag comprises RF powered passive accelerometer; and a plurality of passive secondary RFID tags tagged to a plurality of secondary objects placed in proximity to the at least one primary object, wherein one or more secondary objects from a plurality of secondary objects, required to be used by the subject while performing one or more secondary activities associated with each ADL among the plurality of ADLs to perform each ADL without presence of anomaly, are predefined. Furthermore, the method includes analyzing the RF data received from the at least one battery less wearable tag over a plurality of window intervals to tag the primary activity of the subject, for each window interval, to an ADL among the plurality of ADLs. Thereafter, the method includes analyzing the RF data received from the plurality of passive RFID tags of interest over each of the window interval to detect the one or more secondary activities performed by the subject using the one or more secondary objects and interaction of the subject with the one or more secondary objects corresponding to the tagged primary activity. Furthermore, the method includes and determining presence of anomaly in each window interval if the tagged primary activity of each window interval and the interaction of the subject with the one or more secondary objects in the detected one or more secondary activities for each window interval maps to a predefined primary object and secondary object usage criteria, wherein the predefined criteria is set for confirming expected execution of the ADL among the plurality of ADLs.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
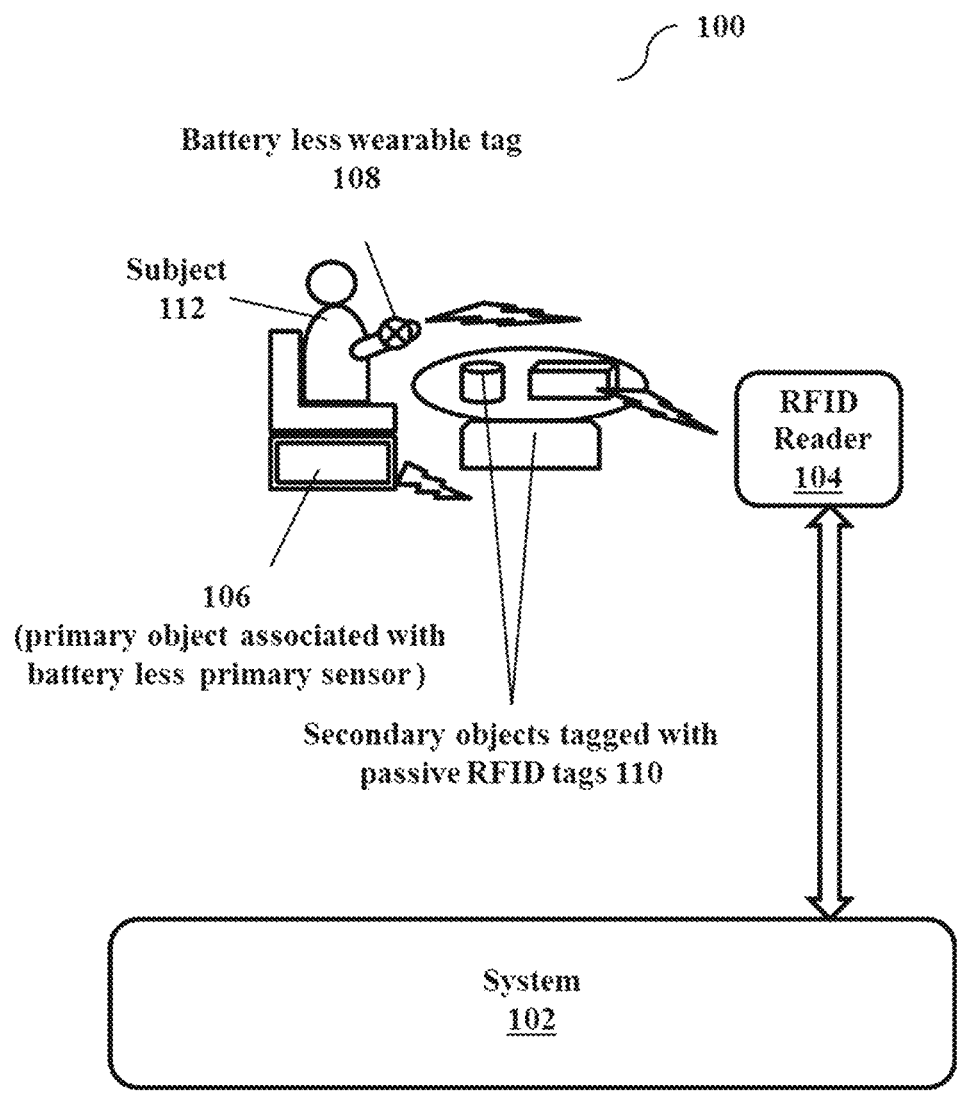
FIG. 1 illustrates an exemplary overview of an architecture for energy efficient activity recognition and behavior analysis, in accordance with embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

The embodiments herein provide a method and system for energy efficient activity recognition and behavior analysis. The architecture disclosed utilizes a hybrid mode of inexpensive, battery-free sensing of physical activities performed by a subject been monitored during his Activities of Daily Living (ADLs). The sensing combines object interaction sensing with person-specific wearable sensing to recognize individual activities in smart spaces (such as a home or office). The method and system disclosed quantifies a probabilistic approach that uses longitudinal observations of user-item interactions, over each individual episode, to compute the anomalous behavior of the subject, alternatively referred as a user. In the approach disclosed, an anomaly is defined not just by the presence or absence of an ADL (e.g., eating), but analyzing the ADL as combination of a primary activity and one or more secondary activities. Thus, for an example ADL such as eating, the method monitors a primary activity of sitting on a chair that indicates subject has initiated the ADL of interest. However, the method further monitors whether the one or more secondary activities are performed. For example, monitoring the secondary activity related to usage of glass during a meal is performed to expectation. Typically say, whether the user interacted with his/her glass multiple times during a meal. This enables to identify what was the performance metric of the subject during the ADL. Thus method provides monitoring beyond mere detecting object oriented ADL. To mention few applications of the method, such fine-grained anomalies identified by the system enable better quantifying the onset or progression of cognitive impairments, for example in health conditions like dementia in elderly users.

Referring now to the drawings, and more particularly to FIGS. 1 through 5, where similar reference characters denote corresponding features consistently throughout the figures, there are shown preferred embodiments and these embodiments are described in the context of the following exemplary system and/or method.

FIG. 1 illustrates an exemplary overview of an architecture 100 for energy efficient activity recognition and behavior analysis, in accordance with embodiments of the present disclosure. The architecture 100 comprises a system 102 energy efficient activity recognition and behavior analysis for a subject 112 under observation, who's various Activities of Daily Living (ADLs) need to be monitored. The manner in which each activity from the plurality of ADLs is to be performed is well defined in the system 102 in terms of one or more primary objects related to the primary activity of an ADL and one or more secondary objects (also referred as environment objects) associated with one or more secondary activities associated with the same ADL.

As depicted in the architecture 100, a hybrid sensing mechanism comprises a plurality of types of sensors and a Radio Frequency Identification (RFID) reader 104 to read data from these sensors.

a) One type of sensor is a battery less wearable tag 108 worn by the subject 112. This for example, can be an accelerometer tag that requires high powered operation of the RFID-reader. The use of a battery less wearable tag permits low-cost, individual specific sensing (such tags currently cost $10-12, two orders of magnitude lower than wearable smart watches), without the need to remove it periodically for recharging.

b) One or more battery less primary sensors (for example, a battery less primary sensor 106) attached to one or more primary objects (for example, chair).

c) A plurality of secondary passive RFID tags attached to the plurality of secondary objects (for example, glass, book, and the like).

In an embodiment, the subject 112 may be asked to wear one or more battery less wearable tags based on the complexity of actions involved in the ADL, alternatively referred as activity, to be monitored. Further, as depicted in FIG. 1, a primary object 106 (for example herein, chair), refers to (mandatory) object to be used by the subject 112, to initiate and perform and expected primary activity for an ADL among the predefined ADLs. To monitor the subject 112 while performing the ADL and determine whether the ADL is performed with or without any anomaly, the system 102 is configured to recognize the primary activity to been performed along with analysis of manner of usage of one or more secondary objects 110 by the subject 112 in the corresponding one or more secondary activities of the primary activity.

As depicted in architecture 100, to determine an activity such as Activity for Daily Living (ADL) and behavior of the subject 112 been monitored, the system 102 identifies an environment of the subject 112 being monitored with help of primary objects and secondary object in the environment of the subject while subject initiates and performs the activity. The subject 112 wears the battery less wearable tag 108, typically an RFID accelerometer that can provide signals or data corresponding to subject's movement. To monitor and record the activity performed by the subject, data from the battery less wearable tag 108 is read by a sensing element of the architecture 100, which is equipped with the RFID reader 104. For the battery less wearable tag a passive RFID tag with a built-in 3-axis accelerometer, for example Farsens Kineo™ can be used.

The RFID reader is a hardware device, usually stationary, and uses RF waves to power the RFID tags, and gather required RF data from various RF sensors within its coverage. Example RFID readers include ThinkMagic™, Astra EX™ and the like. In general, an RFID reader needs to operate in high power mode to read data from RFID tags around, thus for seamless monitoring power consumption of the RFID reader 104 is expected to be high as the RFID readers continuously have to operate in high power mode, draining the battery of the RFID reader 104, effectively disrupting seamless monitoring. This is one major hurdle faced by existing system that monitor ADLs. However, with the system 102 disclosed herein, the RFID reader 104 may be fixed at a location within the environment of the architecture 100 and is set by the system 102 to normally operate in a low power mode. The RFID reader 104, even though in low power mode, is capable of reading data from the primary sensor 106 associated with the primary object (chair). Thus, system 102, does not set the RFID reader 104 in high power mode unless and until and an event is detected. For example, the event may be detection of the primary activity indicating initiation of the ADL by the subject 112. Detection of the event is sensed through the battery less primary sensor 106, which is a RFID passive external sensor tag. For example, the architecture 100 utilizes, a pressure (piezoelectric) sensor under the chair, to help identify when the subject 112 sits on it. This external pressure sensor is connected to a passive RFID tag (e.g., SL900A passive RFID tag), which can be read by the RFID reader 104 in low power mode. The assembly of external pressure sensor and the RFID tag together is referred as the battery less primary sensor 106. On detection of the event, the system 102 is configured to trigger the RFID reader to high power mode, wherein the RFID reader is now capable of reading RF data from any RFID tags around, such as the battery less wearable sensor 108 and/or a plurality of passive RFID tags 110 attached to the plurality of secondary objects 110.

The primary sensor can be battery less force or pressure sensors tagged to one or more primary objects in the environment. The primary objects are objects that are required or mandatory to be used by the subject 112 to perform activities classified as primary activities which further are classified into one or more secondary activities. For example, a primary object may be a chair associated with primary activity of 'sitting'. The primary activity, when performed can be detected by the RFID reader 104 in low power mode by readings seamlessly scanned data from one or more primary sensors 108 in the environment, lying within its RF range.

However, the primary activity of 'sitting' may further include a secondary activity of 'drinking' or 'reading a book or 'both'. The secondary activities thus are associated or performed by the subject using one or more secondary objects 110, which are environmental objects (EOs) such as a cup, a book and the like. Each environmental object is tagged using passive RFID tags, alternatively referred as object tags, which are standard passive RFID tags. The disclosed system 102, utilizes the primary activity detection indicated by the primary sensor 106 as event to trigger monitoring the secondary activity and triggers the high power mode of the RFID reader 104. Since then secondary activity monitoring starts. Further, monitoring of secondary activity is through reading of the passive RFID tags 110 tagged to the secondary objects that provide gestural activity indication of the subject 112. In the high power mode of the RFID reader 104 (*a*) collects of RF data from the plurality passive RFID tags 110 associated with the secondary objects in environment of the subject and (b) collects RF data from the battery less wearable 108 worn by the subject 112. The system 102 then performs analysis of the RF data collected by the RFID reader 104 from the RFID passive tags 110 of the secondary objects and the battery less wearable sensor 108 to identify a specific gesture-driven activity (ADL comprising the primary activity and one or more secondary activities) of the subject 112. Further the system 102 performs window analysis to record current activity of the subject 112 for every window interval of observation. The system 102 further performs episode analysis by analyzing the RF data received from the at least one battery less wearable tag (108) worn by the subject and the plurality of passive RFID tags (110) tagged to a plurality of secondary objects. For recorded activities over larger period such days or months to detect abnormal behavior exhibited by the subject 112. The window analysis and episode analysis are explained in conjunction with flow diagram of FIGS. 3A and 3B.

Figure 2:
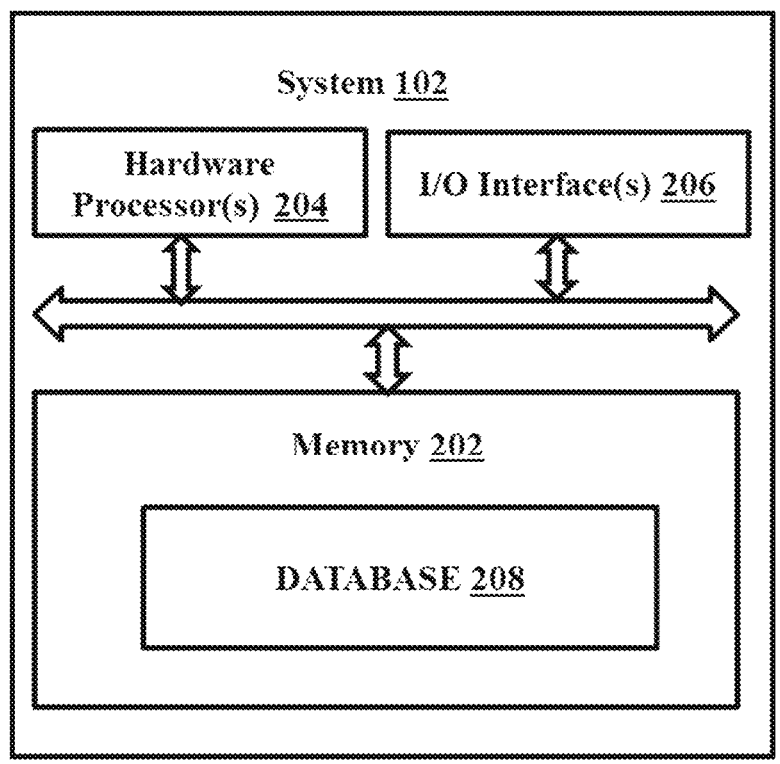
FIG. 2 is a functional block diagram of a system depicted in FIG. 1 providing energy efficient activity recognition and behavior analysis, in accordance with some embodiments of the present disclosure.

FIG. 2 is a functional block diagram of a system depicted in FIG. 1 providing energy efficient activity recognition and behavior analysis, in accordance with embodiments of the present disclosure.

In an embodiment, the system 102 includes processor 204, communication interface device(s), alternatively referred as or input/output (I/O) interface(s) 206, and one or more data storage devices or memory 202 operatively coupled to one or more hardware processor (s) 204, alternatively referred as processor 204. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the system 102 can be implemented in a variety of computing systems, such as laptop computers, notebooks, hand-held devices, workstations, mainframe computers, servers, a network cloud and the like.

The I/O interface(s) 206 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server. The I/O interface 206, is configured to receive (a) the sensor data from the at least one battery less primary sensor 106 associated with at least one primary object, (b) RF data from the at least one battery less wearable tag 108 worn by the subject 112 and (c) RF data from the plurality of passive RFID tags 110 tagged to the plurality of secondary objects placed in proximity to the at least one primary object via the RFID reader 104.

The memory 202 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment the memory 202, may include activity recognizer (not shown in FIG. 2) to recognize the activity (ADL) performed by the subject 112. Also, the memory 202 may include a window analyzer (not shown) further comprising an object scanner (not shown), to perform window analysis providing current activity (short term behavior) of the user over the window or window interval of observation. Also, the memory 202 may comprise an episode analyzer (not shown) to identify long term behavior over a predefined window intervals spanning several days or a month time span. Further, the memory 202 includes a database 208 that may store predefined ADLs. The memory 202, may further store the results of the window analyzer is and the episode analyzer for analysis by an expert and generation of alert notification to an attendant of the subject over an SMS.

In an embodiment, the data base 208 may be external (not shown) to the system 100 and accessed through the I/O interfaces 106. The memory 202 may further comprise information pertaining to input(s)/output(s) of each step performed by the processor 204 of the system 100 and methods of the present disclosure.

Figure 3A:
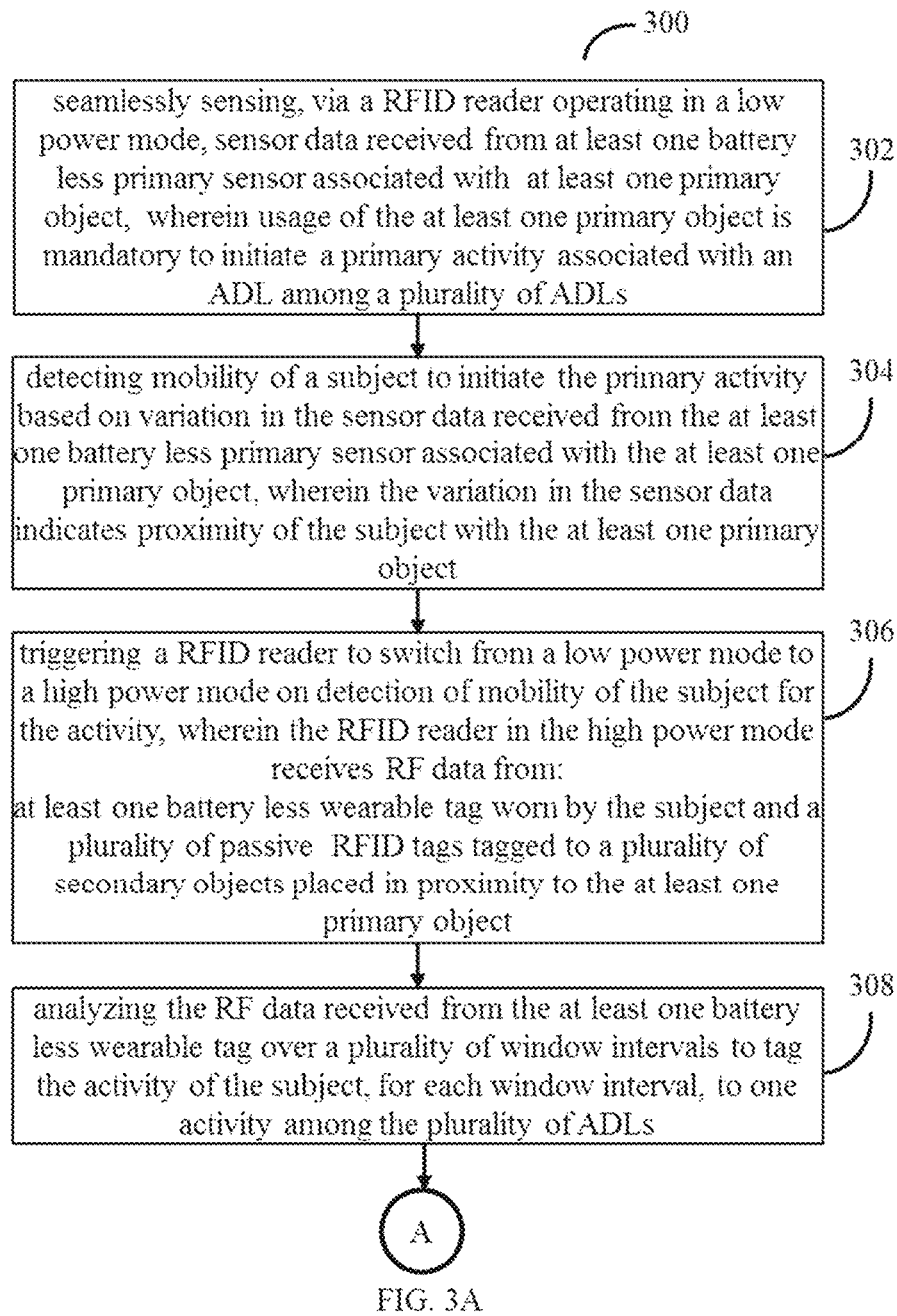
FIG. 3A and FIG. 3B are a flow diagram illustrating a method for energy efficient activity recognition and behavior analysis, in accordance with some embodiments of the present disclosure.
Figure 3B:
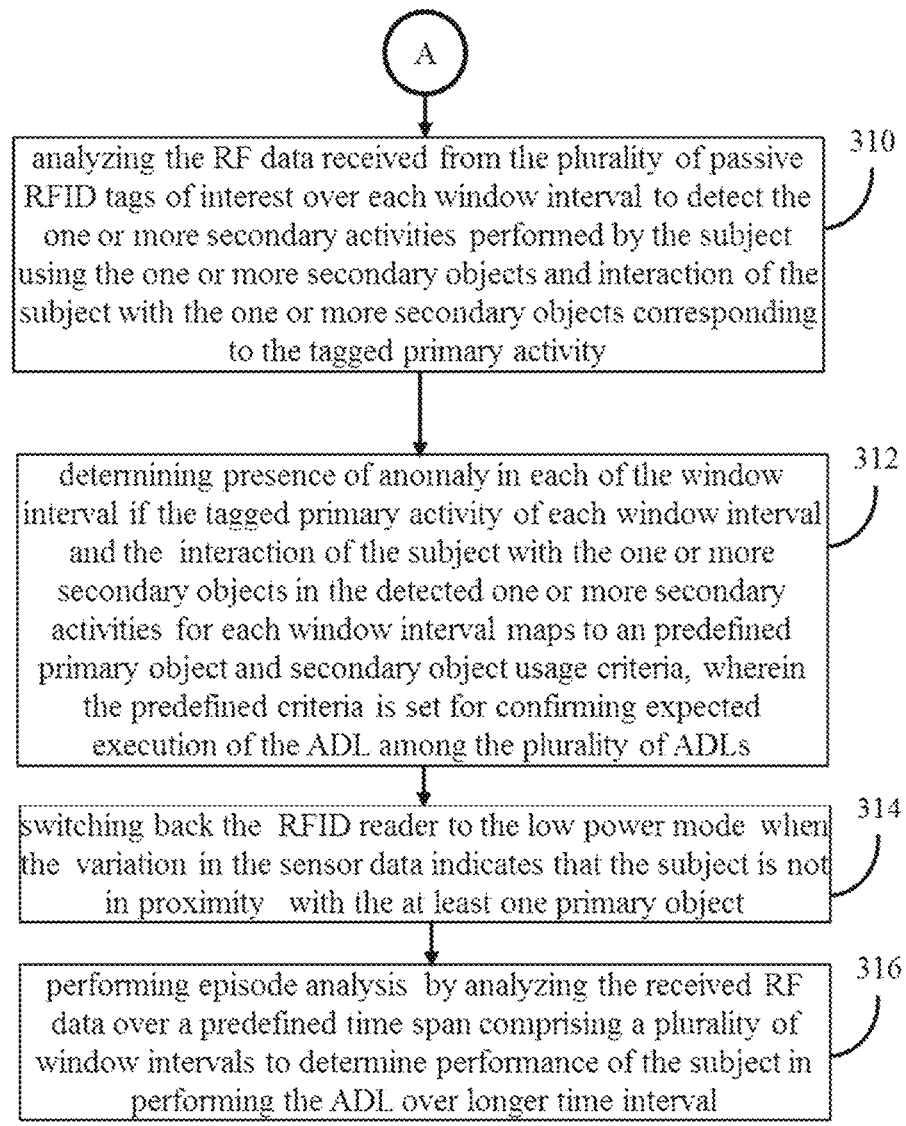
Figure 4A:
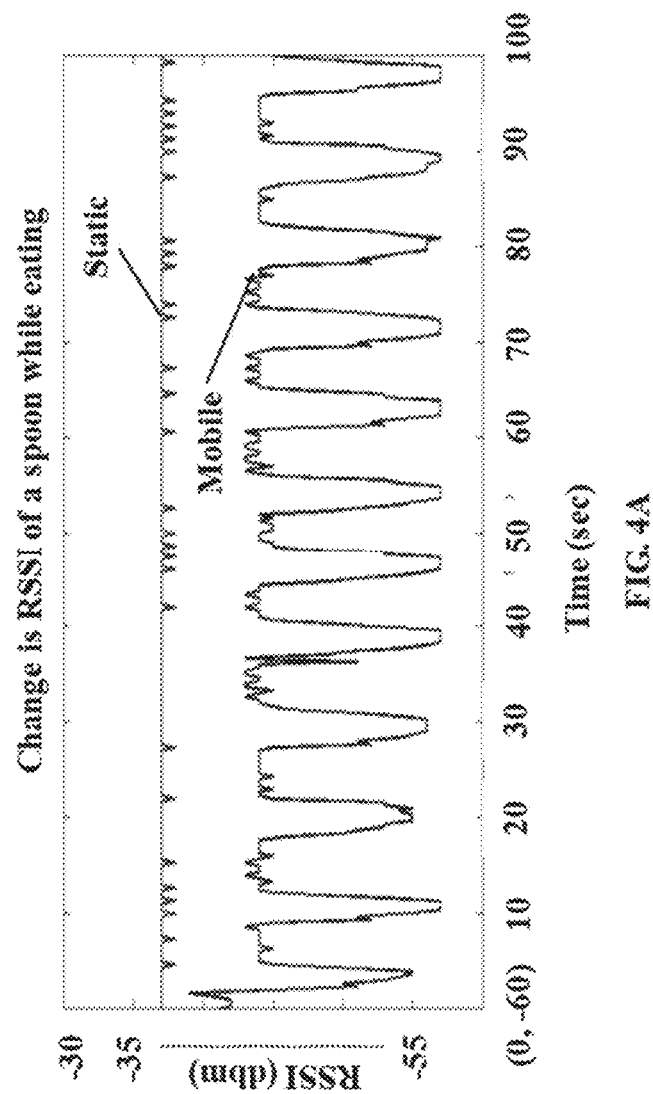
FIGS. 4A, 4B, and 4C illustrate graphical representations of various Activities of Daily Living (ADLs) performed by a subject monitored by the system of FIG. 1, in accordance with some embodiments of the present disclosure.
Figure 4B:
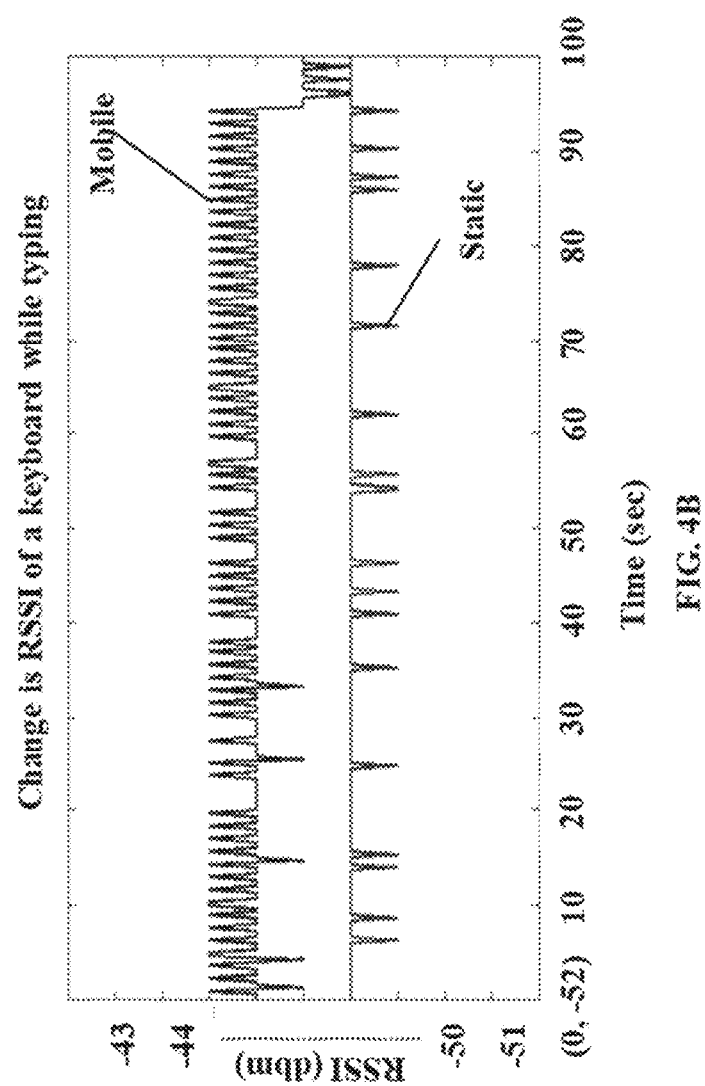
Figure 4C:
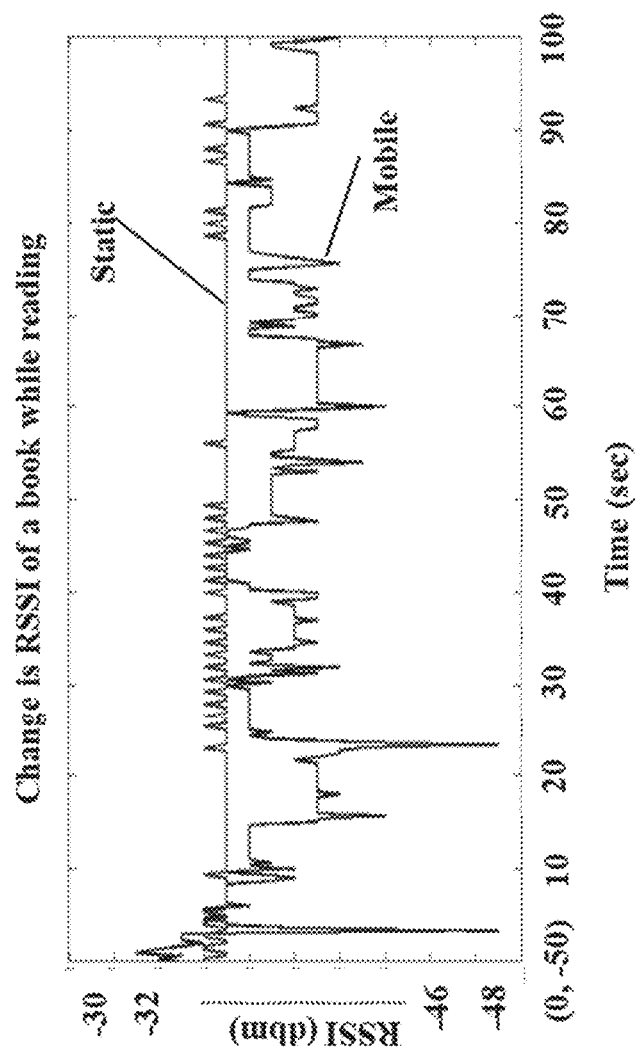

FIG. 3A and FIG. 3B are a flow diagram illustrating a method 300 for energy efficient activity recognition and behavior analysis, in accordance with some embodiments of the present disclosure.

In an embodiment, the system 102 comprises one or more data storage devices or the memory 202 operatively coupled to the processor 204 and is configured to store instructions for execution of steps of the method 300 by the processor 204. The steps of the method 300 of the present disclosure will now be explained with reference to the components or blocks of the system 102 as depicted in FIG. 2 and the steps of flow diagram as depicted in FIG. 3. Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

Referring to the steps of the method 300, in an embodiment of the present disclosure, at step 302, the processor 204 is configured to seamlessly sense, via the RFID reader 104 operating in the low power mode, sensor data received from at least one battery less primary sensor 106 associated with at least one primary object. As mentioned in FIG. 1, usage of the at least one primary object 106 is mandatory to initiate the primary activity associated with an ADL from a plurality of Activities of Daily Living (ADLs).

Referring to the steps of the method 300, at step 304, the processor 204 is configured to detect mobility of the subject 112 associated with initiation of the primary activity based on variation in the sensor data received from the at least one battery less primary sensor 106 associated with the at least one primary object. The variation in sensor data indicates proximity of the subject with the at least one primary object.

Referring to the steps of the method 300, at step 306, the processor 204 is configured to trigger the RFID reader 104 to switch from the low power mode to the high power mode on detection of mobility of the subject 112 for the primary activity. The RFID reader 104 in high power mode receives RF data from:

(a) at least one battery less wearable tag 108 worn by the subject, wherein the at least one battery less wearable tag comprises RF powered passive accelerometer; and (b) a plurality of passive RFID tags tagged to a plurality of secondary objects placed in proximity to the at least one primary object, wherein one or more secondary objects required to be used by the subject while performing each ADL among the plurality of ADLs, without presence of anomaly, are predefined.

Referring to the steps of the method 300, in an embodiment of the present disclosure, at step 308, the processor 204 implementing the activity recognizer is configured to analyze the RF data received from the at least one battery less wearable tag 108 over a plurality of window intervals so as to tag the primary activity of the subject, for each window interval, to one activity among the plurality of ADLs. The function described in step 308 are implemented using the activity recognizer. An analytical framework below further explains the activity recognition process of the activity recognizer.

Referring to the steps of the method 300, in an embodiment of the present disclosure, at step 310, the processor 204 implementing the window analyzer and the object scanner, is configured to analyze the RF data received from the plurality of passive RFID tags of interest over each of the window interval to detect a plurality of secondary activities performed by the subject based on the plurality of secondary objects and interaction of the subject with the secondary objects during the primary activity. The function described in step 310 are implemented using the window analyzer (not shown) also comprising the object scanner. The general analytical framework below further explains the window analysis process Referring to the steps of the method 300, in an embodiment of the present disclosure, at step 312, the processor 204, is configured to determine presence of anomaly in each of the window interval, if the tagged primary activity of each window interval and interaction of the subject 112 with the detected secondary objects in the plurality of secondary activities for each window interval maps to a predefined criteria set. The predefined criteria, for example can be: for a meal (ADL), chair (the primary object) is mandatory to be used indicating initiation of the primary activity sitting) along with usage of a first secondary object (glass) at least one time and usage of a second secondary object (spoon) at least 10 times. The actions of subject related to use of secondary objects are the secondary activities associated with the ADL (meal)). This mapping confirms expected execution of the ADL among the plurality of ADLs.

Referring to the steps of the method 300, in an embodiment of the present disclosure, at step 314, the processor 204, is configured to switch back the RFID reader to the low power mode when the variation in the sensor data indicates that the subject is not in proximity with the at least one primary object.

Referring to the steps of the method 300, in an embodiment of the present disclosure, at step 316, the processor 204 implementing the episode analyzer, is configured to perform episode analysis by analyzing the received RF data over a predefined time span comprising a plurality of window intervals to determine performance of the subject in performing the ADL over longer time interval. The analytical framework for the activity recognizer is explained below.

In an embodiment, the method 300 may further comprise generating an alert notification on detection of presence of the anomaly for corresponding window interval as well as reporting episode analysis to an expert for further analysis and actions, over an email or an SMS on a communication device.

A generic analytical framework implemented by the system 102 post detection of the primary activity for computation of anomalous ADLs is provided below. For a given setting, let A denote the activity grammar such that:

$$A = \{A1, A2, \ldots, Ai, \ldots, An | n \in R\} \quad (1)$$

Where, n denotes the total number of ADLs being monitored.

Data collected from the accelerometer tag (battery less wearable sensor 108) is buffered to obtain a window of data for a fixed duration (i.e. window interval size denoted by ws). Once the window of data is obtained, an exponential smoothing filter is applied to eliminate noise and artifacts, and then identify the user's (subject's) current activity.

Activity Recognition (Step 308):

To predict the current activity, a set of statistical features such as mean, variance of individual axis, co-variance and correlation taking 2 axis at a time and magnitude of all 3 axis is computed for each window of incoming data. The feature vector is first analyzed to identify immobility of the subject, using a binary classifier. If the subject is classified as mobile, a random forest classifier (previously trained in supervised fashion) is used, to predict the current activity label. Let Ak denote output activity label from the machine learning model for the kth window of data.

Object Scanner (Step 310):

In parallel to the activity recognition functionality, the object scanner (window analysis functionality) analyzes the data from the passive object tags (passive RFID tags 110) to identify the presence of, and interaction with, different secondary objects in the environment (secondary objects). For window analysis, the environment is sensed in parallel with the battery less wearable sensor 108. Let X denote the collection of such secondary objects:

$$X = \{X1, X2, \ldots, Xn\} \forall Xi \in X; \quad (2a)$$

$Xi = 1$: when object is present (i.e., the tag is read)

$$= 0; \text{ when object is absent} \quad (2b)$$

Here, the system 102 assumes that activity Ai is performed using object Xi. Furthermore, all the activities Ai are independent of each other and an activity Ai can be performed with or without the object Xi. There might be cases, where the secondary objects may be present in the scene but are not used. To monitor the usage of the secondary objects, the system 102 utilizes change in Received Signal Strength Indicator (RSSI) values of the passive RFID tags 110. Graphical representation of the received RSSI values depicted in FIG. 4A, FIG. 4B and FIG. 4C indicate how the RSSI values changes when secondary objects are being used (are in motion or mobile) as in (a) eating or (b) typing, when compared objects are not used (static). The system 102 utilizes a binary classifier, using features such as the variance and standard deviation of the RSSI of the reflected signal from each secondary tag, to identify whether a specific secondary object is being used or not used. The secondary object usage output is then fused with gesture based activity recognition for a corresponding window interval. Furthermore, keeping a track of such secondary object usage, in a long run can serves as metadata for anticipating activity of a person (subject). For example, if a person (subject) uses a particular cup for drinking tea and also water during medicine intake then from this relationship the system can trigger activity models for that object, using the personalized usage pattern.

Window-Wise Analysis (Step 312):

Outputs from the activity recognition flow and the object scanner are then analyzed to detect if the current window is an anomaly or not. A window is said to be an anomaly, if the object Xi is not present or is present but not used while performing activity Ai (only secondary objects that have a high support in the training data, i.e. actively used in training episodes of an ADL, are considered for such anomaly determination.

A window is annotated as anomaly only when Xi=0, or if Xi=1, and the object scanner asserts that the object Xi is not used. Let ZW be defined as the anomaly status for a given window.

$ZW=0$: when $Xi=1$ and object is used.

=1: otherwise. (3)

The output of the window analyzer is a collection of windows and its anomaly status. Let W denote the collection of activity windows such that:

$$W=\{W1,W2,\ldots Wk|k\in R\} \quad (4a)$$

$$Wk=<Ak,ZWk>|Ak\in A \quad (4b)$$

Where, k denotes the time index of a window, Ak is output activity label assigned to that time window, and ZWk is the corresponding anomaly status.

Episode-Wise Analysis (Step 316):

With 'W' as an input, this episode analysis functionality or module computes episode occurrence of different activities and corresponding episode anomalies (if any). This stage of analysis is performed offline on a longitudinal basis (at the end of every day, every month and so on). Episode of an activity is computed based on the average time duration Ti for Ai to occur. Let T be a collection of such duration values Ti, $$T=\{T1,T2,\ldots,Ti,\ldots,Tn\} \quad (5)$$

Let C be a collection of threshold count for each of the n activities, denoting the minimum number of windows to be predicted as label Ai, in time Ti so that the system detects it as an episode occurrence of Ai. Empirically it can be assumed that this threshold count should be somewhere within one standard deviation (σi) from the average duration of the episode for activity Ai.

$$C=\{c1,c2,\ldots cn|ci=(Ti-\sigma i)/Ws\} \quad (6)$$

Computing an Episode:

For activity detection window size ws and for a given activity Aj, let Ti be the duration of episode. Hence the total number of windows will be (Ti*60 sec)/ws, out of which if ci windows are classified as Ai then an episode of activity Ai has occurred. This computation of episode is done in post processing block. Let E denote the collection of all episodes in a day.

$$E=\{E1,E2,\ldots Ej|j\in R\} \quad (7a)$$

$$Ej=<Ai,ZEj> \quad (7b)$$

Where, Ej is jth episode detected in a given day further denoted by a tuple of activity label Ai, for which the episode occurred and its anomaly status as ZEj Identifying Episode Anomaly:

Once a collection of windows is identified as an Episode, each such episodes are analyzed for identifying Episode Anomaly (EA). If a majority of windows of the activity Ai in that episode are annotated as window anomaly, then that episode is considered as an anomaly denoted by ZE as follows:

$ZE=1$: when $ZWk=1$ for majority of windows in $E$

=0: otherwise (8)

Inference Engine:

A collection of all such episodes are analyzed every end of the day, to check if even a single episode anomaly is detected for any given activity (Ai). When an episode anomaly is detected, certain probability values (given below) are calculated and stored for future analysis and inference purposes.

$$P(Ei) = \frac{\text{number of } EA\text{'s for activity }(Ai)}{\text{Total number of } Ai \text{ episodes in a day}} \quad (9a)$$

$$P(E) = \frac{\text{number of } EA\text{'s}}{\text{Total number of episodes in a day}} \quad (9b)$$

Where, P indicates the fraction of episodes (for activity Ai) that were performed without using the tagged object. A very low probability value indicates that the person has used the tagged objects for doing most of his activities, whereas high value indicates a deviation from the normal conduct of such an ADL. On the other hand, P (E) gives an overall probabilistic measure of the subject's regularity in using appropriate objects while performing their usual ADLs.

Figure 5:
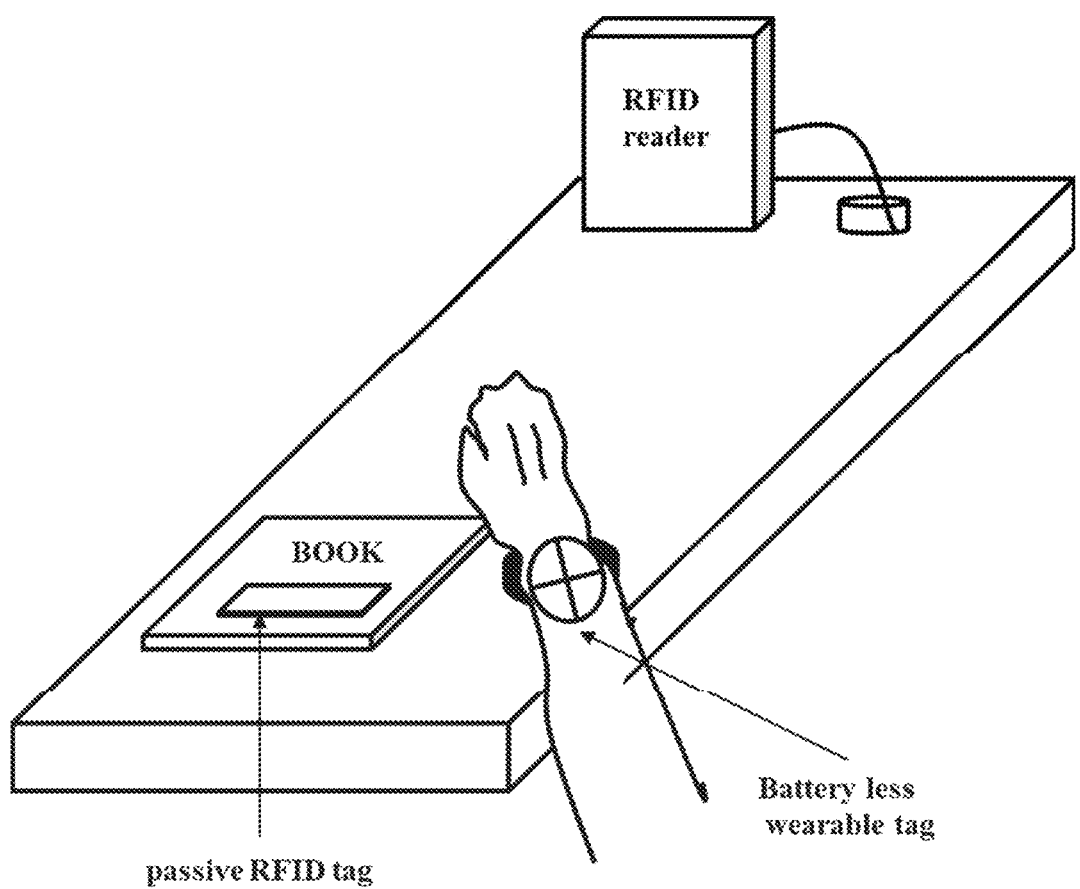
FIG. 5 illustrates an experimental set up for the system of FIG. 1, in accordance with some embodiments of the present disclosure.

FIG. 5 illustrates an experimental set up for the architecture 100 of the FIG. 1 comprising the system 102, in accordance with some embodiments of the present disclosure. A use case, referred as Table of Interest (as shown in FIG. 5) is a scenario of rehabilitation center, consisting of a table and chair, where most of the important daily chores are performed. Here the chair is the object that defines the sitting context and anticipated activities are defined in an activity recognition and behavior analyzer's activity grammar given by A={EATING, TYPING, READING}, i.e. n=|A|=3. A trained machine learning model M is used to perform the activity recognition for a window (ws) of 10 secs. The tagged objects (EOs) include X={SPOON, LAPTOP, BOOK} corresponding to each activity respectively. The sensing system is triggered opportunistically, where the RFID reader in the system works in two power modes a) Low power (at 20 dBm) to read pressure sensor tag place on the chair (primary object) to sense the sitting context and b) High power (at 30 dBm) to read accelerometer tag (Ws) worn by the subject respectively. The system starts at a low power mode to monitor the sitting context. Once the chair (primary object) is occupied, as sensed from PO tag on chair, the power mode is changed to high, as well the environment is scanned for the tagged secondary objects (alternatively referred as environmental object (EOs) with EO tags) present. Real time accelerometer data from the battery less wearable tag 108 worn by the subject 112 is then buffered and analyzed. When the subject leaves, the RFID reader 104 fails to read accelerometer data from the battery less wearable tag 108. To ensure this, a sanity check made via the state of the pressure sensor (PO tag) on chair. In absence of the subject, the RFID reader 104 is switched to low power mode, else an error alert is triggered.

Experimental Results:

Experiments were conducted for the above mentioned use case. All the data were collected in lab environment1. The participants were asked to wear the wearable tag, get seated on a chair and perform 5 minutes of each activity, i.e., Eating, Typing and Reading (as shown in FIG. 5). As soon as the pressure sensor could sense the occupancy of a subject, accelerometer data was sensed using RFID reader (sampling rate 5 Hz) and logged as different files for individual activities. Data collection involved 20 healthy subjects. Features were computed for every 10 sec window and Random forest classifier is used to generate a trained model. Table 1 gives the confusion matrix for a 10-fold cross validation testing, with an accuracy of 96%.

TABLE 1

Confusion Matrix

|  | Eating | Reading | Typing |
|---|---|---|---|
| Eating | 531 | 13 | 7 |
| Reading | 6 | 543 | 19 |
| Typing | 2 | 19 | 514 |

The learned model is also tested in real time deployment with 5 unknown test subjects performing 3 minutes of activity (1 min for each activity, back to back) with a sequence of eating, typing and reading. The mean average error (MAE) computed considering each activity individually were 0, 0.2 and 0.17 respectively. It can be observed during the experiment that the windows which involved a transition from one activity to another, were sometimes incorrectly classified hence contributing to the total MAE 0.12. The RSSI based, object usage binary classifier is trained using 3 objects. RSSI data is collected from the passive RFID tags in different states, when in use and when not in use. A 10-fold cross-validation reported an accuracy of 82% using a random forest classifier.

The system 102, provides a battery less wearable along with an object tracking framework that utilizes low cost, battery less RFID tags to support fine-grained ADL recognition, providing a new design choice in the spectrum of "physical analytics" technologies. By using moderately large window size values of 10 secs, the system 102 can distinguish the three ADLs with high accuracy. The system 102 can be used to study the micro-level object interactions of users while performing ADLs, thereby providing a way to monitor changes in a user's orderliness over time. Such orderliness measures, based on microscopic human-object interactions, may provide valuable insight in anticipating the onset or progress of cognitive ailments (e.g., dementia) in elderly patient.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software processing components located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various components described herein may be implemented in other components or combinations of other components. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method for activity recognition and behavior analysis, the method comprising:
seamlessly sensing, via one or more hardware processors using a Radio Frequency Identification (RFID) reader operating in a low power mode, sensor data received from at least one battery less primary sensor associated with at least one primary object, wherein usage of the at least one primary object is mandatory to initiate a primary activity associated with an ADL among a plurality of Activities of Daily Living (ADLs);
detecting, via the one or more hardware processors, mobility of a subject to initiate the primary activity based on variation in the sensor data received from the at least one battery less primary sensor associated with the at least one primary object, wherein the variation in the sensor data indicates proximity of the subject with the at least one primary object;
triggering, via the one or more hardware processors, the RFID reader to switch from the low power mode to a high power mode on detection of mobility of the subject for the primary activity, wherein the RFID reader in the high power mode receives RF data from:
at least one battery less wearable tag worn by the subject, and wherein the at least one battery less wearable tag comprises a RF powered passive accelerometer; and
a plurality of passive RFID tags tagged to a plurality of secondary objects placed in proximity to the at least one primary object, wherein one or more secondary objects from a plurality of secondary objects, required to be used by the subject while performing one or more secondary activities associated with each ADL among the plurality of ADLs to perform each ADL without presence of anomaly, are predefined;
analyzing, via the one or more hardware processors, the RF data received from the at least one battery less wearable tag over a plurality of window intervals to tag the primary activity of the subject, for each window interval, to an ADL among the plurality of ADLs;
analyzing, via the one or more hardware processors, RF data received from the plurality of passive RFID tags of interest over each window interval to detect the one or more secondary activities performed by the subject using the one or more secondary objects and interaction of the subject with the one or more secondary objects corresponding to the tagged primary activity; and
determining, via the one or more hardware processors, presence of anomaly in each of the window interval if the tagged primary activity of each window interval and the interaction of the subject with the one or more secondary objects in the detected one or more secondary activities for each window interval maps to a predefined primary object and secondary object usage criteria, wherein the predefined criteria is set for confirming expected execution of the ADL among the plurality of ADLs.

2. The method of claim 1, further comprising switching back, by the one or more hardware processors, the RFID reader to the low power mode when the variation in the sensor data received from the at least one battery less primary sensor indicates that the subject is not in proximity with the at least one primary object.

3. The method of claim 1, further comprising performing episode analysis, by the one or more hardware processors, by analyzing the received RF data, received from the at least one battery less wearable tag worn by the subject and the plurality of passive RFID tags tagged to a plurality of secondary objects, over a predefined time span comprising a plurality of window intervals to determine performance of the subject in performing the ADL over longer time interval.

4. The method of claim 1, further comprising generating, by the one or more hardware processors, an alert notification on detection of presence of the anomaly during execution of the ADL for corresponding window interval.

5. A system, comprising:
a memory storing instructions;
one or more Input/Output (I/O) interfaces; and
one or more hardware processors coupled to the memory via the one or more I/O interfaces, wherein the one or more hardware processors are configured by the instructions to:
seamlessly sense via Radio Frequency Identification (RFID) reader operating in a low power mode, sensor data received from at least one battery less primary sensor associated with at least one primary object, wherein usage of the at least one primary object is mandatory to initiate a primary activity associated with an ADL among a plurality of Activities of Daily Living (ADLs);
detect mobility of a subject to initiate the primary activity based on variation in the sensor data received from the at least one battery less primary sensor associated with the at least one primary object, wherein the variation in the sensor data indicates proximity of the subject with the at least one primary object;
trigger the RFID reader to switch from the low power mode to a high power mode on detection of mobility of the subject for the primary activity, wherein the RFID reader in the high power mode receives RF data from:
at least one battery less wearable tag worn by the subject, wherein the at least one battery less wearable tag comprises a RF powered passive accelerometer; and
a plurality of passive RFID tags tagged to a plurality of secondary objects placed in proximity to the at least one primary object, wherein one or more secondary objects from a plurality of secondary objects, required to be used by the subject while performing one or more secondary activities associated with each ADL among the plurality of ADLs to perform each ADL without presence of anomaly, are predefined;
analyze the RF data received from the at least one battery less wearable tag over a plurality of window intervals to tag the primary activity of the subject, for each window interval, to an ADL among the plurality of ADLs;
analyzing, via the one or more hardware processors the RF data received from the plurality of passive RFID tags of interest over each window interval to detect the one or more secondary activities performed by the subject using the one or more secondary objects and interaction of the subject with the one or more secondary objects corresponding to the tagged primary activity; and
determining, via the one or more hardware processors, presence of anomaly in each of the window interval if the tagged primary activity of each window interval and the interaction of the subject with the one or more secondary objects in the detected one or more secondary activities for each window interval maps to a predefined primary object and secondary object usage criteria, wherein the predefined criteria is set for confirming expected execution of the ADL among the plurality of ADLs.

6. The system of claim 5, wherein the one or more hardware processor is further configured to switch back the RFID reader to the low power mode when the variation in the sensor data received from the at least one battery less primary sensor indicates that the subject is not in proximity with the at least one primary object.

7. The system of claim 5, wherein the one or more hardware processors are further configured to perform episode analysis by analyzing the received RF data over a predefined time span comprising a plurality of window intervals to determine performance of the subject in performing the ADL over longer time interval.

8. The system of claim 5, wherein the one or more hardware processors are further configured to generate an alert notification on detection of presence of the anomaly during execution of the ADL for corresponding window interval.

9. A non-transitory computer readable medium, the non-transitory computer-readable medium stores instructions which, when executed by a hardware processor, cause the hardware processor to perform actions comprising:

seamlessly sensing using a Radio Frequency Identification (RFID) reader operating in a low power mode, sensor data received from at least one battery less primary sensor associated with at least one primary object, wherein usage of the at least one primary object is mandatory to initiate a primary activity associated with an ADL among a plurality of Activities of Daily Living (ADLs);

detecting mobility of a subject to initiate the primary activity based on variation in the sensor data received from the at least one battery less primary sensor associated with the at least one primary object, wherein the variation in the sensor data indicates proximity of the subject with the at least one primary object;

triggering the RFID reader to switch from the low power mode to a high power mode on detection of mobility of the subject for the primary activity, wherein the RFID reader in the high power mode receives RF data from:

at least one battery less wearable tag worn by the subject, and wherein the at least one battery less wearable tag comprises a RF powered passive accelerometer; and a plurality of passive RFID tags tagged to a plurality of secondary objects placed in proximity to the at least one primary object, wherein one or more secondary objects from a plurality of secondary objects, required to be used by the subject while performing one or more secondary activities associated with each ADL among the plurality of ADLs to perform each ADL without presence of anomaly, are predefined;

analyzing the RF data received from the at least one battery less wearable tag over a plurality of window intervals to tag the primary activity of the subject, for each window interval, to an ADL among the plurality of ADLs;

analyzing RF data received from the plurality of passive RFID tags of interest over each window interval to detect the one or more secondary activities performed by the subject using the one or more secondary objects and interaction of the subject with the one or more secondary objects corresponding to the tagged primary activity; and determining presence of anomaly in each of the window interval if the tagged primary activity of each window interval and the interaction of the subject with the one or more secondary objects in the detected one or more secondary activities for each window interval maps to a predefined primary object and secondary object usage criteria, wherein the predefined criteria is set for confirming expected execution of the ADL among the plurality of ADLs.

10. The non-transitory computer readable medium of claim 9, further comprising switching back, by the one or more hardware processors, the RFID reader to the low power mode when the variation in the sensor data received from the at least one battery less primary sensor indicates that the subject is not in proximity with the at least one primary object.

11. The non-transitory computer readable medium of claim 9, further comprising performing episode analysis, by the one or more hardware processors, by analyzing the received RF data, received from the at least one battery less wearable tag worn by the subject and the plurality of passive RFID tags tagged to a plurality of secondary objects, over a predefined time span comprising a plurality of window intervals to determine performance of the subject in performing the ADL over longer time interval.

12. The non-transitory computer readable medium of claim 9, further comprising generating, by the one or more hardware processors, an alert notification on detection of presence of the anomaly during execution of the ADL for corresponding window interval.

* * * * *